US006805841B2

(12) United States Patent
Shvets et al.

(10) Patent No.: US 6,805,841 B2
(45) Date of Patent: Oct. 19, 2004

(54) LIQUID PUMPING SYSTEM

(75) Inventors: Igor Shvets, Dublin (IE); Dmitri Kashanin, Dublin (IE); Vivienne Williams, Gorey (IE)

(73) Assignee: The Provost Fellows and Scholars of the College of the Holy and Undivided Trinity of Queen Elizabeth Near Dublin, Dublin (IL)

( * ) Notice: Subject to any disclaimer, the term of this patent is extended or adjusted under 35 U.S.C. 154(b) by 462 days.

(21) Appl. No.: 09/851,375

(22) Filed: May 9, 2001

(65) Prior Publication Data

US 2002/0182113 A1 Dec. 5, 2002

(51) Int. Cl.[7] .................. G01N 21/64; G01N 21/00; G01N 7/00; G01N 30/02; G01N 23/48
(52) U.S. Cl. .................. 422/100; 422/50; 422/103; 422/104; 422/63; 422/68.1; 422/81; 422/99; 436/43; 436/174; 436/180
(58) Field of Search .................. 422/50, 100, 103, 422/104, 68.1, 63, 81, 99; 436/43, 174, 180; 417/1, 44.9, 52; 137/1

(56) References Cited

U.S. PATENT DOCUMENTS

| | | |
|---|---|---|
| 3,923,426 A | 12/1975 | Theeuwes et al. |
| 4,137,913 A | 2/1979 | Georgi |
| 4,715,786 A | 12/1987 | Wolff et al. |
| 4,908,112 A | 3/1990 | Pace |
| 5,171,132 A | 12/1992 | Miyazaki et al. |
| 5,224,843 A | 7/1993 | Van Lintel |
| 5,242,408 A | 9/1993 | Jhuboo et al. |
| 5,630,706 A | 5/1997 | Yang |
| 5,632,876 A | 5/1997 | Zanzucchi et al. |
| 5,656,034 A | 8/1997 | Kochersperger et al. |
| 5,759,014 A | 6/1998 | Van Lintel |
| 5,779,868 A | 7/1998 | Parse et al. |
| 6,062,681 A * | 5/2000 | Field et al. .................. 347/65 |
| 6,063,589 A | 5/2000 | Kellogg et al. |
| 6,277,257 B1 * | 8/2001 | Paul et al. .................. 204/450 |
| 6,524,456 B1 * | 2/2003 | Ramsey et al. .................. 204/450 |
| 6,615,856 B2 * | 9/2003 | McNeely et al. .................. 137/14 |

FOREIGN PATENT DOCUMENTS

JP   4058074 A   2/1992

* cited by examiner

*Primary Examiner*—Jill Warden
*Assistant Examiner*—Brian Sines
(74) *Attorney, Agent, or Firm*—Birch, Stewart, Kolasch & Birch, LLP

(57) ABSTRACT

A liquid outlet link assembly is provided for liquid delivery output rates below 10 μl per minute so as to smooth out the flow from a positive displacement pump which has an immediate step pumping rate which is relatively substantially larger than the delivery rate required through the liquid outlet means. Essentially, this liquid link assembly has a bubble of air or some other pressure activated expansion means which initially contracts on the step pump such as a syringe pump operation and then gradually expands over time, allowing a steady output rate through the link assembly.

54 Claims, 12 Drawing Sheets

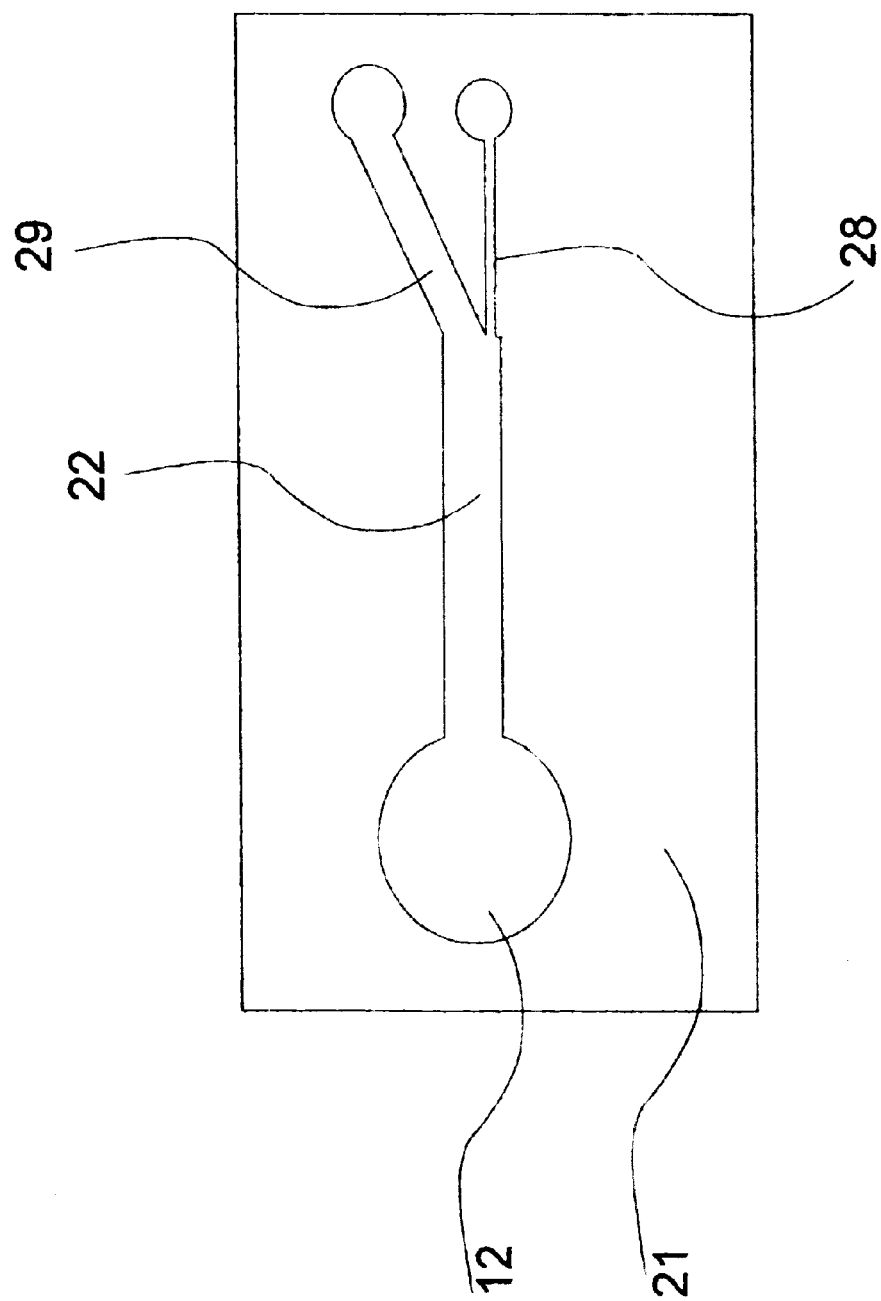

LIQUID PUMPING SYSTEM

BACKGROUND OF THE INVENTION

1. Field of the Invention

The present invention relates to liquid flows and, in particular, liquid flows at relatively slow speeds within relatively small bores such as those of microchannel structures or microcapillaries. The invention further relates to a liquid outlet link assembly for such liquid flows and to a microchannel structure assembly for microfluidic systems.

2. Background of the Invention

In recent years, microminiaturized fluidic systems are used extensively in analytical chemistry, drug discovery and life sciences. Microchannel structures of 20–100 $\mu$m in cross section are used in chemistry to achieve fast speed electrophoretic separation for chromatography. These structures, often referred to as bioelectronic chips or bio chips, could offer a convenient method of isolating, lysing, and detecting of micro-organisms in complex samples and could have applications in drug discovery, genetic testing and separation sciences (e.g. capillary electrophoresis).

For chemistry and drug discovery microfluidic reactors, microchannel structures and microcomponents present the possibility of decreasing the time of technological processes by integrating several units in relatively small areas. This could facilitate the execution of a number of reactions in parallel and increase efficiency in high throughput screening and combinatorial analysis. Overall, sample volumes within microcomponents are in the microliters range, which can save considerably on the amounts of reagents per reaction. For successful control of microreactors, efficient detection and separation of chemical specimens, it is absolutely necessary to provide fluid delivery at the low flow rates.

In the area of life sciences, the study and manipulation of single biological cells on microfluidic structures could potentially enable considerable experimental progress Manipulation of cells is becoming important for clinical diagnostics and genetic measurements. Lysing of cells, cell-cell interaction, interaction and manipulation of a single cells is now possible and it is more efficient using microchannel structures. It is expected that integrated analytical systems will allow genetic measurements and drug screening at the single cell level.

In these wide areas of application of microstructures, pumping systems play a significant role. Delivering required solutions to the sites of reaction, mixing different fluids, creating gradients of concentration of the reagents, controlling the positions of biological samples, transporting and manipulating them are all tasks, which require a highly accurate pumping system. Despite a major effort in developing pumping systems for a microchannel structure, the problem still remains. Many conventionally used pumping systems are operating with significantly bigger volumes of fluids, therefore they cannot provide pumping accuracy or in some cases adequate pumping speed when it comes to establishing flows inside the microstructures with a microchannel diameter from 5 to 100 $\mu$m.

DESCRIPTION OF PRIOR ART

Various constructions of positive displacement pumps, including syringe pumps, positive pressure infusion pumps and peristaltic pumps have been used with capillaries. These are, for example, described in U.S. Pat. No. 4,715,786 (Wolff et al. Syringe pumps with microflow rate capabilities to provide precise and reproducible volumetric flow ranges of the order of 0.1 $\mu$l to 1 ml per minute have been described, for example, in U.S. Pat. No. 5,630,706 (Yang) and U.S. Pat. No. 5,656,034 (Kochersperger et al). One of the main objects of these inventions has been to deliver pulse free flow, the problem being that the pressure of the fluid inside the syringe pump changes during the stroke of the syringe pump, which stroke is usually controlled by a stepper motor. Unfortunately, such an operation results in a large pressure surge which alters the volumetric flow rate. For example, Japanese Patent Specification No. 4058074A (Nagataka et al) describes a method to reduce fluctuations of the flow in a syringe pump to provide a more stable flow rate by setting the syringe vertically and forming a gas layer between the front surface of the piston forming the syringe pump and the liquid being pumped. This invention, however, is directed towards relatively large flow rates of the order of microliters per minute and would be useful for drug infusion but would not be particularly suitable for microchannel structures and the like, where the flow rates are, as mentioned already, substantially less.

U.S. Pat. No. 4,137,913 (Georgi) describes a method of controlling the flow rate by changing the stroke periods. U.S. Pat. No. 5,242,408 (Jhuboo et al) describes a method of controlling pressure inside a syringe pump by measuring the force acting on the plunger and detecting an occlusion. Unfortunately, heretofore, such syringe and positive displacement pumps are relatively inefficient at delivering fluid flow at rates of the order of nanoliters per minute, which flow rate is required to transport liquids in microchannel structures. Generally, the limitation on the flow rate is the movement accuracy of the various mechanical parts of the syringe pump such as the stepper motor, plunger, valves, and so on. However, syringe pumps used in high pressure liquid chromatography (HPLC) have achieved volumetric flow rates as low as 0.1 $\mu$l/min. A typical example of this is described in U.S. Pat. No. 5,630,706 (Yang). However, for commercially available syringe pumps, the linear displacement of the piston or plunger would be several micrometers per step of the motor controlling the pump. Thus, general sealing surface wear makes it impossible to achieve accuracy for shorter displacements.

A further disadvantage of the syringe pump when used for pumping fluids in microchannel structures, is that it cannot deliver a sufficiently low pumping speed for many applications of the structures.

Typically, a syringe pump would dispense 0.6 $\mu$l/min for one step of the motor which then has to be delivered into a microchannel structure possibly having a cross sectional diameter of the order of 40 $\mu$m which translates into 1.9 mm/sec. through the microchannel structure which is much too fast for the observation of biological specimens, detection of proteins, single cells and the creation of low gradients of reagents, which is required in many microfluidic applications. Indeed, one can readily appreciate that at this speed, visual observation is difficult and further would not allow for the manipulation or sensing of biological samples. Thus, heretofore, positive displacements pumps and in particular, syringe pumps, while very attractive for their simplicity, have not as of yet been useful for these applications.

Electrokinetic pumps have been proposed for such pumping operations. Pumps based on electroosmotic phenomena have been described in U.S. Pat. No. 3,923,426 (Theeuwes et al) and U.S. Pat. No. 5,779,868 (Wallace Parce et al). When a buffer is placed inside a capillary, the inner surface of the capillary acquires a charge. This is due to the ionisation of the wall or adsorption of ions from the buffer.

In the case of silicate glass, the surface silanol groups (Si—OH) are ionised to silanoate groups (Si—O⁻). These negatively charged groups attract positively charged cations from the buffer, which form an inner layer of cations at the capillary wall. These cations are not in sufficient density to neutralize all the negative charges, therefore a second layer of cations forms. The inner layer of cations, strongly held by the silanoate groups, forms a fixed layer. The second layer of cations is less strongly held because it is further away from the negative charges, threfore it forms a mobile layer. When an electric field is applied, the mobile layer is pulled toward the cathode. Since ions are in solution, they drag the whole buffer solution with them and cause electroosmotic flow. The distribution of charges due to the formation of charged layers create a potential termed the zeta potential.

This method, originally used for capillary electrophoresis, is recently being used for fluid transport in microstructures and for high speed chromatography in microfluidic chips. However, it still has a number of disadvantages.

The distribution of charges and formation of layers depends on the initial charge of the inner surface of the capillary, which is different for various materials and solutions used. Moreover, it can be reliant on the pH history of the capillary. This makes the control of the zeta potential and therefore electroosmotic flow control a complicated task. The prior art evidences a number of ways to treat the capillary in order to achieve a reproducible flow rate. They indicate that coating the microcapillary with a monomolecular layer of non-cross-linked polyacrylamide can derivatize inner surfaces of a capillary. This coating enhances the osmotic effect and suppresses adsorption of solutes on the walls of the capillary. Others have taught that altering the buffer pH, the concentration of the buffer, the addition of surface-active components, such as surfactants, glycerol, etc. or adding various organic modifiers to the buffer solution may alter electroosmotic flow. In some cases this alteration can cause a reverse of electroosmotic flow or its complete cancellation.

Transport of particles in electroosmotic pumping systems is also difficult, due to the fact that during transport they can acquire an electrical charge and can be moved by the electric field, which in some cases causes flow to reverse.

According to the theory, the mobile layer drags the fluid. As a result electroosmotic flow has a relatively flat flow profile i.e. the flow velocity is rather uniform across the capillary. When a static pressure is opposed to the electroosmotic flow, the resulting flow can produce a turbulence, which doesn't allow controllable mixing of fluids and biological samples and decreases speed of electroosmotic flow.

For example, U.S. Pat. No. 4,908,112 (Pace et al) suggests the use of electro-osmotic pumps to move fluids through channels less than 100 microns in diameter. A plurality of electrodes was incorporated in the channels, which were etched into a silicon wafer. An electric field of about 250 volts/cm was required to move the fluid to be tested along the channel. However, when the channel is long, a large voltage needs to be applied to it, which may be impractical for highly integrated structures. This US patent specification suggests that the electrodes be staggered to overcome this problem, so that only small voltages could be applied to a plurality of electrodes. However, this requires careful placement and alignment of a plurality of electrodes along the channel.

Electrohydrodynamic (EHD) pumping of fluids is also known and may be applied to small capillary channels. The principle of pumping here is different from electroosmosis. When a voltage is applied, electrodes in contact with the fluid transfer charge to or from the fluid, such that fluid flow occurs in the direction from the charging electrode to the oppositely charged electrode. Electrohydrodynamic (EHD) pumps can be used for pumping resistive fluids such as organic solvents. U.S. Pat. No. 5,632,876 (Zanzucchi Peter John et al) describes the use of both electroosmotic and electrohydrodynamic fluid movement method to establish flow in microcapillaries for polar and non-polar fluids.

One of common problems that is usually encountered in these two types of fluid pumping system is the appearance of gas bubbles, which are easily obtained during pumping as a result of electrolysis. They normally interfere with particle transport, blocking microstructures; requiring additional pressure difference to transport them. Pumping of fluids by pumps based on electroosmosis and electrohydrodynamic phenomena relies on the electrical contact throughout the fluid, which disappears in the presence of bubbles rendering pumping by these methods difficult.

Another method of fluid transport in a microfluidic structure is by mechanical micropumps and valves incorporated within the structure such as described in U.S. Pat. No. 5,224,843 (Van Lintel), U.S. Pat. No. 5,759,014 (Van Lintel) and U.S. Pat. No. 5,171,132 (Miyazaki et al).

As described in U.S. Pat. No. 5,759,014 (Van Lintel), the operation of these pumps is greatly influenced by the compressibility of the fluid and the presence of an air bubble inside the pumping chamber. The pumping speed decreases in the presence of a significant air bubble, sometimes even reducing to zero. Procedures of priming these pumps is complicated and requires a vacuum pump or special injection devices, to prevent appearance of bubbles in the micropumps main pumping chamber. Therefore, it is also impractical to use micropumps as a part of disposable microfluidic biochips.

Another method of pumping fluids in microchannel systems is based on centrifugal force caused by rotation of the microchannel structures at desired speed. In a most common embodiment, the microchannel structure is a disk in a format similar to that of a CD platform. The fluid in this case flows from the centre of rotation to the periphery. Due to opposing surface tension and centrifugal forces at the interface between the fluid medium and air, it is possible to implement an rpm-dependent valves and switches. Therefore this method provides a way to facilitate sequential reactions on chip platform. In U.S. Pat. No. 6,063,589 (Kellogg Gregory et al), the microsystem platforms are described as having microfluidics components, resistive heating elements, temperature sensing elements, mixing structures, capillary and sacrificial valves, as well as methods for using these microsystem platforms for performing biological, enzymatic, immunological and chemical assays. A rotor with a slip ring capable of transferring electrical signals to and from the microsystem platforms is also described in the invention.

While such centrifugal pumps can provide required flow rates in microfluidic systems and integrate components on a single platform, this method has a number of shortcomings. The fluids can only be transported in one direction and no reversed flow is possible. Control of the flow rate in the individual channels is not possible dynamically, but only by designing a specific geometry of the microchannel structures. Therefore mixing is only possible with predefined ratios. Replacement of one of the fluids for a fluid with a different viscosity requires a change in the design of the structure. The valves can only operate only ones when interface between fluid and air presents inside the valve. For the complicated interconnected channel geometries during the filling process air bubbles may appear in some places. This would require an additional increase in the rotation to pump them and therefore would lead to non-reliable experiments particularly in the case of sequentially executed experiments. This is opposed to pressure pumps where multiple pumps can facilitate a filling process individually for each channel, if required. When a microfluidic structure is rotated at a high speed it becomes impossible to visually observe biological samples, which is very important for a number of applications, for example for the study of cellular responses.

Despite several types of pump methods proposed for pumping fluids in the microchannel structures, there is no simple solution, which can be used in many of the applications utilizing microchannel structures. All methods have some disadvantages, which are more or less significant for different applications. For example, it's not practical to use micromachined pumps in applications of disposable biochips. Integration micromachined pumps with a disposable device would increase the cost of it. In the same example electroosmotic pumps cannot provide a great degree of reliability. It seems to be impractical when every disposable chip needs to be treated before experiment in order to successfully control electroosmotic velocity.

OBJECTS OF THE INVENTION

The present invention is directed towards providing a pumping system and method for pumping liquids in microchannel structures to enable an accurate control of flow for flow rates ranging from 100 picoliters per minute to 10 microliters per minute. Such a system should be suitable for pumping both conductive and non-conductive liquids and in particular, for pumping liquids with different viscosities and liquids which contain particles with sizes comparable to the microchannel's diameter. Thus, such a pumping system should be suitable for delivering liquids with biological samples.

The invention is also directed towards providing a pumping system and method for pumping liquids which will enable accurate mixing of flows in different microchannel structures in a wide range of concentrations, and in particular to the accurate control of liquid gradients in the microchannels. Further, the invention is directed towards providing a pumping system and a method for pumping liquids in microchannel structures which can be accurately controlled either by an operator or in response to some condition of the liquid such as, for example, a speed of reaction or indeed some other phenomenon.

SUMMARY OF THE INVENTION

The invention provides a liquid outlet link assembly to provide a steady liquid delivery output rate below 10 $\mu$l per minute. This liquid output rate is for delivery through a liquid outlet from a positive displacement pump. Generally, such a positive displacement pump has an immediate step pumping rate which is substantially larger than the delivery rate through the liquid outlet means. Thus, the liquid outlet means has greatly reduced delivery compared to that of the positive displacement pump. The invention provides this liquid outlet link assembly which is a body with a resistance of flow therethrough substantially less than through the liquid outlet means which can be anything from a microcapillary or any such similar system. There is a liquid inlet in the body of the link assembly for connection to the pump and an outlet in the body for connection to the liquid outlet means and a pressure activated expansion means in the body to create a liquid pressure at the liquid outlet to provide the desired liquid delivery flow through the liquid outlet means. Generally, the expansion means comprises a gas bubble and more likely a bubble of air. The volume of the bubble is many multiples of the liquid dispensed in one step of the pump. There can be more than one bubble and indeed any air within the liquid link assembly assists in its operation. It is envisaged that the pressure activated expansion means, instead of being a gas or air bubble, could be an elastic membrane forming part of the body member of the link assembly. It could even be that there is expandable tubing in the link assembly. As mentioned above, ideally the liquid outlet means comprises an elongate microchannel structure in which case it is important to have a liquid pressure which is sufficient to provide the necessary liquid pressure gradient between the proximal end of the microchannel structure and the distal end forming the output of the microchannel structure.

Obviously, the invention provides various forms of control, either means for sensing the flow conditions to ensure that the pump operates in response to the sensed flow conditions and this could be any form of optical flow monitoring. It could equally be a pressure sensing means. Further, the invention provides a pump assembly incorporating the liquid link assembly as described above. The pump can be a syringe pump and generally speaking, the volume pump for one step of the syringe pump is greater than 0.1 $\mu$l but could be of the order of 0.2 $\mu$l. It is envisaged that more than one syringe pump may be provided and indeed ideally they dispense different volumes, one of the pumps dispensing a volume many multiples of that of the other pump. An electrokinetic pump can be provided and ideally such an electric pump is an electroosmotic pump or could be an electrohydrodynamic pump.

Further, the invention provides a microstructure assembly which has an internal bore of less than 1000 $\mu$m$^2$ cross-sectional area. Ideally, there is provided a positive displacement pump operating in which each step operation of the pump dispenses a volume of the order of 0.01 $\mu$l. Then again, a liquid link assembly as described above may be used.

It is envisaged that in any liquid link assembly, adjacent the liquid outlet link assembly, there is provided a flow balancing conduit, the cross-sectional area of the body adjacent the inlet substantially equaling the aggregate cross-sectional area of the microchannel structure and the balancing conduit. It can include a liquid take-off means whereby the flow rates of liquid in a liquid link assembly and the liquid outlet means are substantially equal. Thus, where in a microchannel structure, you might have a flow rate normally many multiples of that required in the liquid link assembly to allow the requisite liquid to be delivered through the microchannel structure, by using this flow balancing conduit or other means, the flow rates of both will be substantially the same. For example, the liquid outlet of the body can include a recirculation pipe connected between the liquid outlet and the body of the liquid link assembly.

BRIEF DESCRIPTION OF THE DRAWINGS

The invention will be more clearly understood from the following description of some embodiments thereof, given by way of example only, with reference to the accompanying drawings, in which:

FIG. 12 is a plan view of another microchannel structure.

DESCRIPTION OF THE PREFERRED EMBODIMENTS

Figure 1:
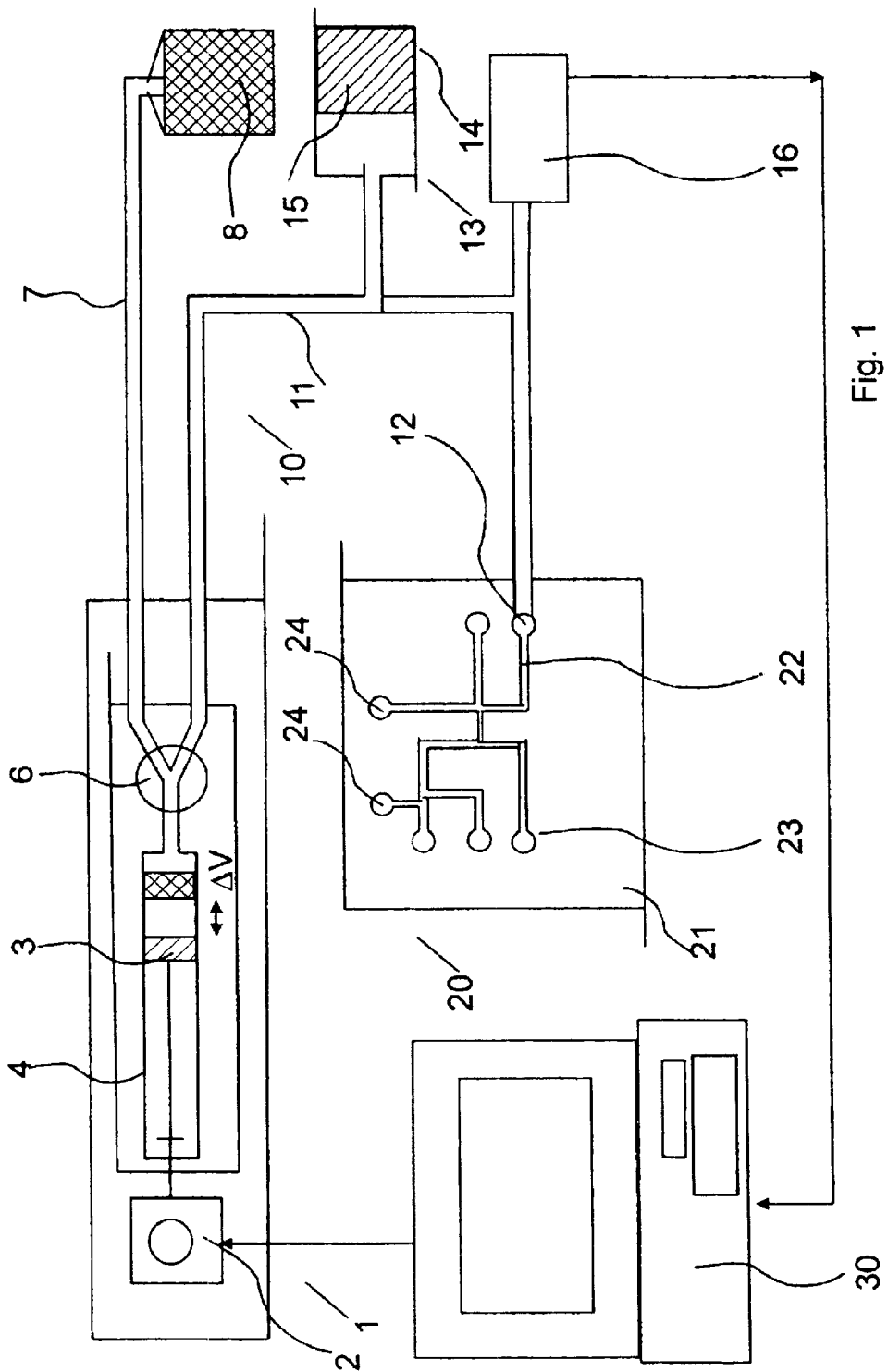
FIG. 1 is a schematic view of a pumping assembly according to the invention.

Referring to the drawings and initially to FIG. 1, there is illustrated a pumping assembly, namely a positive displacement pump, indicated generally by the reference numeral 1, and a liquid outlet link assembly indicated generally by the reference numeral 10, connecting the positive displacement pump 1 with a liquid outlet means, indicated generally by the reference numeral 20. The liquid outlet link assembly 10 and the pump together can form one liquid delivery unit. The positive displacement pump 1 is a syringe pump operated by a stepper motor 2 having a plunger 3 mounted within a syringe body 4. One incremental step of the plunger 3 is identified by the interrupted lines in FIG. 1, which displace a volume ΔV. The plunger 3 is identified by cross-hatched lines and (3) in FIG. 1. The pump 1 feeds a valve 6. The valve 6 is fed by a conduit 7 from a liquid reservoir 8. The valve 6 connects the pump 1 to the liquid outlet link assembly 10.

The liquid outlet link assembly 10 comprises a body having a hollow interior with a resistance to flow therethrough substantially less than through the liquid outlet means 20. The body is formed by a conduit 11. The valve 6 forms a liquid inlet to the body of the link assembly for connection to the positive displacement pump 1. The reference numeral 6 is also used to identify the liquid inlet to the body or conduit 11. A liquid outlet 12 is provided in the liquid link assembly 10. A pressure activated expansion means, indicated generally by the reference numeral 13, is provided by a reservoir 14 containing an air bubble 15, which reservoir 14 is connected to the conduit 11. A pressure sensor 16 is connected to the conduit 11. The liquid outlet means 20 comprises, in this embodiment, a microchannel structure 21 having an entry port which is coincident with the liquid outlet 12 and is identified by the same reference numeral 12 and in turn feeds via a microchannel 22 an exit port 23 in conventional manner. Additional ports 24 are provided. A computer based controller 30 is connected to the stepper motor 2 and the pressure sensor 16 forming the flow sensing means. The resistance to flow through the hollow interior of the body of the liquid outlet link assembly, namely, through the conduit 11, is substantially less than the resistance through the liquid outlet 12, that is to say, through the microchannel 22 of the microchannel structure 21. Further, as will be readily appreciated, the positive displacement pump 1, by its very nature, will have an immediate step pumping rate which is relatively substantially larger than the delivery rate through the liquid outlet means 20.

In operation, when the positive displacement pump 1 operates, there will be an immediate increase in pressure at the valve 6 which is effectively an immediate increase in pressure at the liquid inlet to the body of the link assembly 10. This increase in pressure in the conduit 11 will cause the air bubble 15 to contract and this will immediately reduce the rise in pressure in the conduit 11 and thus at the liquid outlet 12 of the liquid link assembly 10. As a result a steady pressure will be exerted in the liquid outlet means 20, that is to say, the microchannel structure 21. Accordingly, there will no longer be pressure surges within the microchannel structure 21. The pressure sensor 16 and the controller 30 can be used to control the stepping motor 2 and thus the output of the positive displacement pump 1. Any additional air trapped in the link assembly 10 will similarly be compressed.

Essentially then, what the invention does is that it provides a liquid outlet link assembly which provides a steady liquid delivery output rate, usually below 10 μl per minute, through a liquid outlet means. The delivery is from a positive displacement pump having an immediate step pumping rate which is relatively substantially larger than the delivery rate through the liquid outlet means. Effectively, the liquid outlet link assembly smoothes out the delivery from the positive displacement pump. Needless to say, any other suitable positive displacement means could be used other than a syringe pump and that similarly, other arrangements of liquid outlet means, other than microchannel structures, may be used.

Since the controller 30 is connected to both the positive displacement pump 1 and the liquid link assembly 10 via the movement of the positive displacement pump 1, the operation of the valve 6 can be controlled.

Before discussing the operation in any more detail, it is worth discussing briefly, the method of pumping according to the present invention. Essentially, the system comprises three distinct units, namely, the positive displacement pump which operates in a series of steps. This in turn feeds through what is effectively an outlet assembly having the pressure stabilising means which in turn feeds the elongate enclosed microchannel structure. What the bubble does is that it adds expandability and compressibility to the pumping system which allows accurate regulation of pressure at the liquid outlet 12. It will be appreciated that this is contrary to conventional methods where considerable efforts are taken to avoiding and removing air bubbles. One could expect that an expandable inner volume would compromise the dispensing accuracy of the pump and lead to error.

However, this is not the case. As is known, the velocity v of the liquid in a circular capillary under a limitation of laminar flow is subject to Poiselle's law, $$v = \frac{(p_1 - p_2)*r^2}{8*\eta*L},$$

where $p_1$, $p_2$ are pressure values at the inlet and outlet of the capillary, r is the radius of the capillary, η is the viscosity of the fluid, L is the length of the capillary and * indicates multiplication.

The embodiment described above uses a positive displacement pump in combination with this expandable/compressible element formed by the air bubble to produce a small pressure difference between the inlet and outlet port of the microchannel structure and therefore to establish slow movement of the fluid inside the microchannel structure. Once this pressure difference is established in each case the resulting velocity of the liquid would depend on the viscosity of the liquid and diameter and length of the microchannel structure according to Poiselle's Law. For example, for a capillary with a diameter of 50$\mu$m and a length of 20 cm, 5-mbar pressure gradiants will create water flow with mean velocity of about 75 $\mu$m/s.

Suppose, the initial volume of the gas bubble is $V_0$. Suppose then the plunger of the syringe pump moves and expels a volume of the liquid $\Delta V$. If the liquid is enclosed in the unexpandable conduit and the liquid is practically uncompressible, the volume of the air bubble will decrease by essentially the same amount $\Delta V$. At this point, an assumption has been made that the liquid is enclosed, and therefore the liquid outlet is closed and the liquid cannot exit it. This causes an increase in pressure that can be calculated from gas state law, PV=RT, namely, PV=const.:

$$p_0 * V_0 = p_N * (V_0 - \Delta V),$$

$$p_N = p_0 + \Delta p,$$

where $p_N$ is the pressure on the air bubble after the movement of the plunger and $p_0$ is the pressure before the movement. Thus $$\frac{\Delta p}{p_0} = \frac{\Delta V}{V_o - \Delta V}$$

For example if the volume of the bubble is halved: $\Delta V = V_0/2$, the pressure will increase by a factor of two. The ratio of the initial volume of the bubble to the smallest displaced volume within the syringe pump gives the accuracy of building up the pressure at the entry port. The greater is the initial volume of the bubble the higher is the accuracy of the pressure regulation.

In practice the system is not enclosed and is connected to the microchannel structure 22, that is to say, the microcapillary or microstructure. In this case there will be a flow of liquid through the microchannel structure which will cause the volume of the bubble to gradually return to the initial state. However if the volume of the air bubble is several orders of magnitude greater than the volumetric flow rate through the microstructure multiplied by the time of the experiment, the change in the volume of the bubble will be negligible and therefore in pressure at the entry port will be practically constant. In the case when the flow of the liquid through the microchannel structure is causing significant change in pressure, the pressure can be corrected by displacing additional volume of liquid from the syringe pump. Alternatively, for such a case the volume of the air bubble can be increased.

Figure 2:
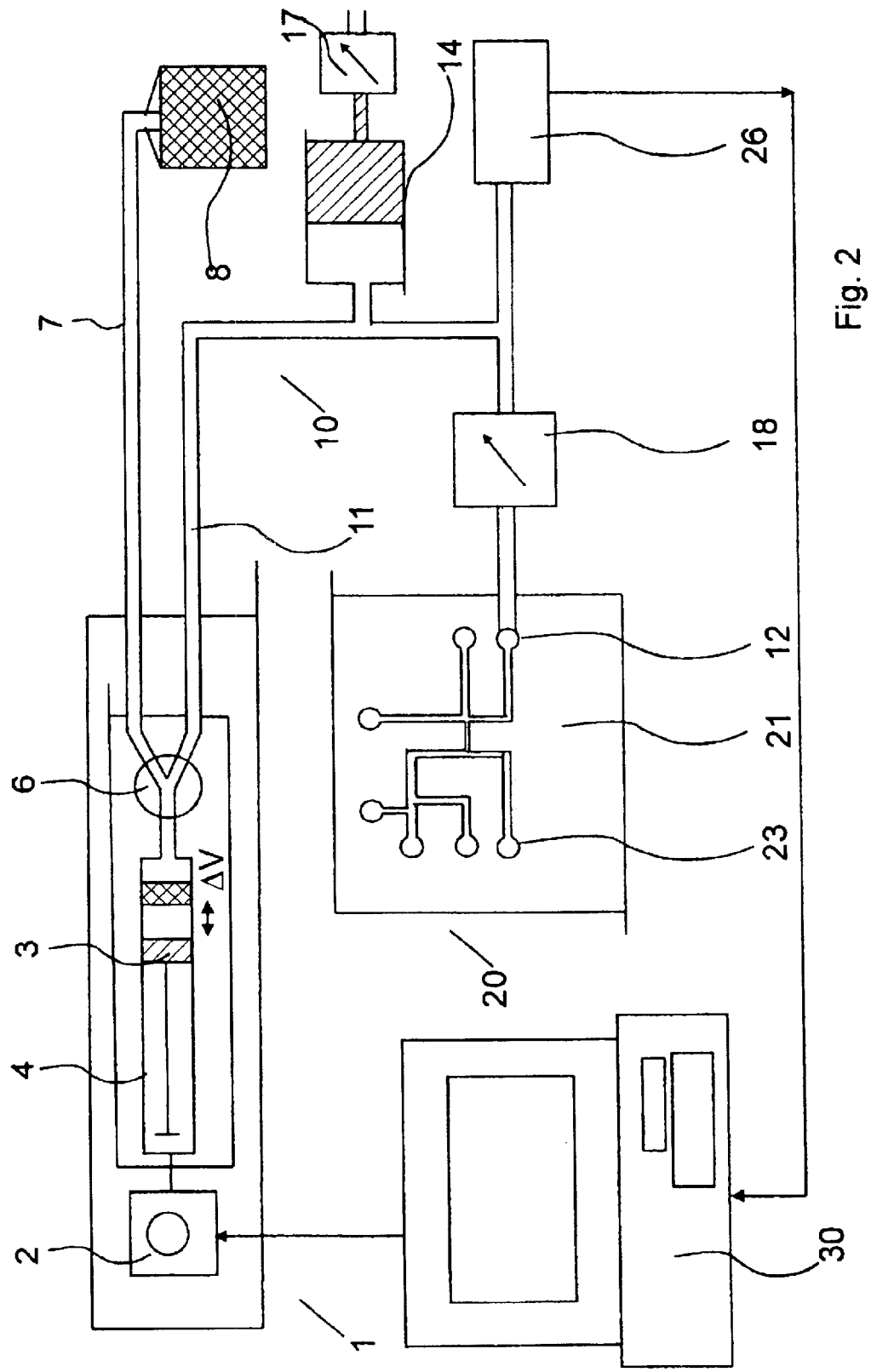
FIG. 2 is a schematic view of an alternative pumping assembly.

Referring now to FIG. 2, there is shown an alternative construction of microchannel structure assembly according to the present invention, substantially similar to the microchannel structure assembly of FIG. 1, in which parts similar to those described with reference to the previous drawings are identified by the same reference numerals. In this embodiment, the air reservoir 14 is provided with an air reservoir valve 17 and the conduit 11 has a control valve 18 adjacent the liquid outlet 12. The valves 17 and 18 are connected to the processor based controller 30.

To compare the ratio between the velocity of the liquid in a system without one containing an air bubble and with one containing an air bubble, initially there was no air bubble in the system, that is to say, the pressure activated expansion means was disconnected and a 100 steps of displacement were applied to the syringe plunger which corresponded to a total displaced volume of 0.2 $\mu$l over a time period of 1 second. Under these conditions, the mean velocity of the liquid in the microchannel structure 21 having a diameter of 10$\mu$m and a length of 20 cm was calculated as follows:

$$v=V/St$$

where v=velocity, V=volume of the liquid expelled by the plunger, S=area of the capillary, t=time taken to expel the liquid.

$$v = V/St = \frac{0.2 \; \mu l}{\pi * (50 \; \mu m)^2 / 4 * 1 \; \text{sec}} \approx 10 \; \text{cm/sec}$$

10 cm/sec is the linear velocity of liquid in a system without pressure compressible means.

When measured with an air bubble in a microchannel structure with a diameter of 50 $\mu$m and a length of 20 cm with an air bubble of 40 $\mu$l, the velocity of liquid was 50 $\mu$m/sec. Therefore, the ratio of velocity in the two systems was $$R = \frac{10 \; \text{cm/sec}}{50 \; \mu m/\text{sec}} = 2000$$

Thus, in accordance with the present invention, it was possible to achieve a velocity of 2000 times lower and a better flow regulation than with the conventional use of a stepper motor. Obviously, if the diameter of the channel of the microchannel assembly is reduced, this will even further increase the velocity in a conventional system without pressure compressible means. On the other hand, the velocity in the system with pressure compressible means according to the present invention will decrease according to Poiselle's law and hence this ratio will increase. If, however, the reverse takes place, then the ratio will decrease. Similarly, should the length of the microchannel structure be increased, this will increase the resistance and hence increase the ratio as the velocity in the microchannel structure will decrease in the system according to the present invention. If, however, the microchannel structure were to be a short channel with large cross section, then there would be no great advantage in using a bubble of air.

We can see from this analysis that the advantage of using pressure compressible means becomes significant when dealing with microfluidic structures. For capillaries with relatively large cross section, pressure compressible means only adds to the error of volume dispensing. An additional Advantage of using pressure compressible means is that it dampens pressure surges. In order to achieve the calculated 10 cm/sec velocity, the large excess pressure must be created at an input of the capillary. Such large pressure surges can be detrimental to certain biological liquids, e.g. cell suspensions. As the flow velocity is reduced according to the example by a factor of 2000 by means of air bubble, the excess pressure is also reduced by the same factor.

Various calculations were carried out to find out whether there was any significant expansion in the conduit and capillary tubing joining the syringe pump and the microchannel structure which was found to be negligible and no particular significance was found from expansion of any other portion of the device. These calculations were performed for typical flexible polymer capillaries of which the conduit of the liquid outlet link assembly is made.

The use of a bubble of air is advantageous as heretofore the removal of air has been a major aim of anybody operating in these systems. Using what effectvely heretofore was something that you did not require and indeed actively tried to eliminate is advantageous. It will be appreciated that other devices for pressure control could be used. A typical example that would be immediately apparent to those skilled in the art, is any form of flexible and elastic membrane. All that is required is to choose the correct material for the membrane and the correct area of it. Also, more sophisticated expansion means and pressure release means could be provided, however, the use of a bubble of air is particularly advantageous.

Calibration of the positive displacement pump 1 and liquid outlet link assembly 10 can be easily carried out by sealing the liquid outlet 12 by closing the liquid inlet valve 18 and the internal volume of the air bubble can then be determined. By displacing different volumes of liquid from the syringe pump and reading the pressure, one can obtain a calibration curve and then by using the formula (1) above, calculate the volume of air in the system. The internal volume of the bubble includes the volume of air in the liquid reservoir 8 and in the system itself. Such air may be trapped in the pump, tubing, valves, etc. There could numerous air pockets around different parts of the liquid link assembly which will not cause any difficult to the operation of the invention in contra distinction to present situations. After calibration, it is possible to adjust the volume of the air in the whole system, thus defining its expandability.

In a typical embodiment, a total volume of 50 $\mu$l of liquid was introduced into the syringe pump. The volume of air bubble was between 40 and 120 $\mu$l. The typical pressure at the entry of the microstructure was 0.5 to 0.1 mbar, the regulation of flow rate being dependent on the parameter of the microstructure. For example, for channels of length 20 cm and diameter of 50 $\mu$m, the corresponding lowest flow rate that could be achieved was 100 pl/min.

Figure 3:
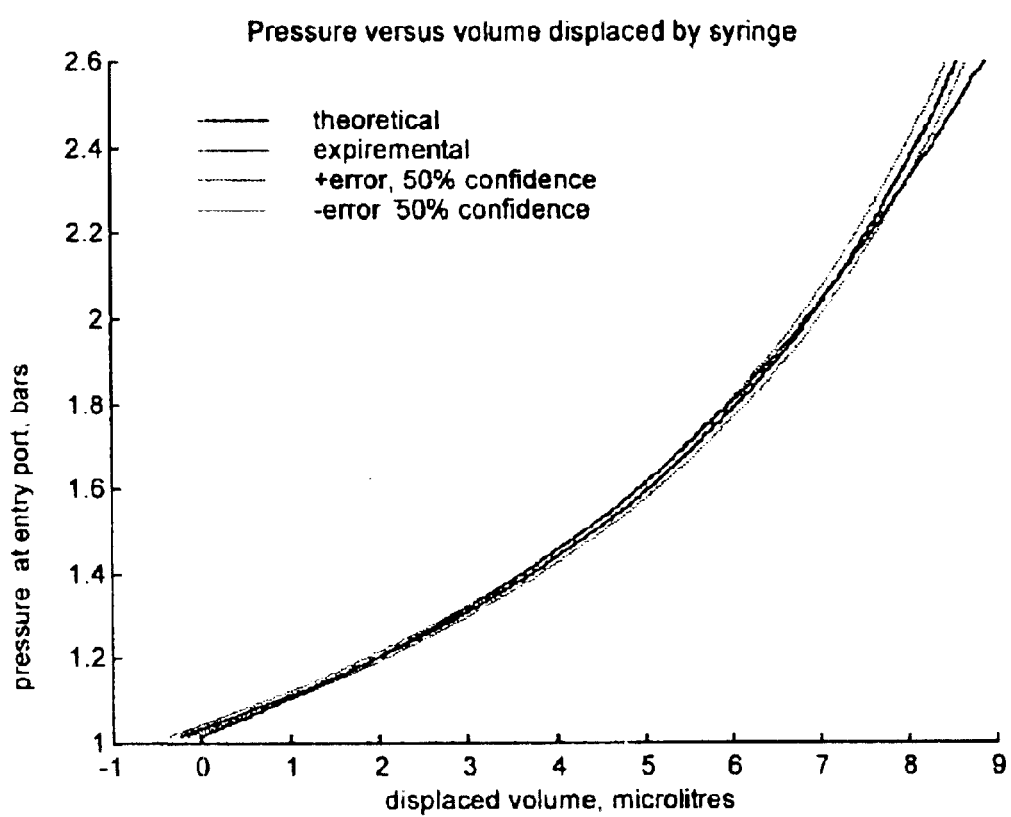
FIG. 3 is a graph showing the results of tests carried out.

FIG. 3 illustrates theoretical and experimental results for the dependence and the pressure at the entry of the microchannel structure on the volume displaced by the syringe pump. This shows that pressure values can be reasonably well predicted. Thus, once the initial pressure and air bubble volume is known, then it is possible to find a required displacement to achieve a desired pressure at the entry port. Again, since $$pV = \text{constant},$$

and $$p = \frac{p_0 V_0}{V_0 - \Delta V} \quad (1)$$

where $\Delta V$ is the displaced volume, $V_0$ is initial volume of the bubble under atmospheric pressure, $p_0$ is the initial pressure, then it is possible, as can be seen, to detect clearly the displacement of the syringe required.

Figure 4:
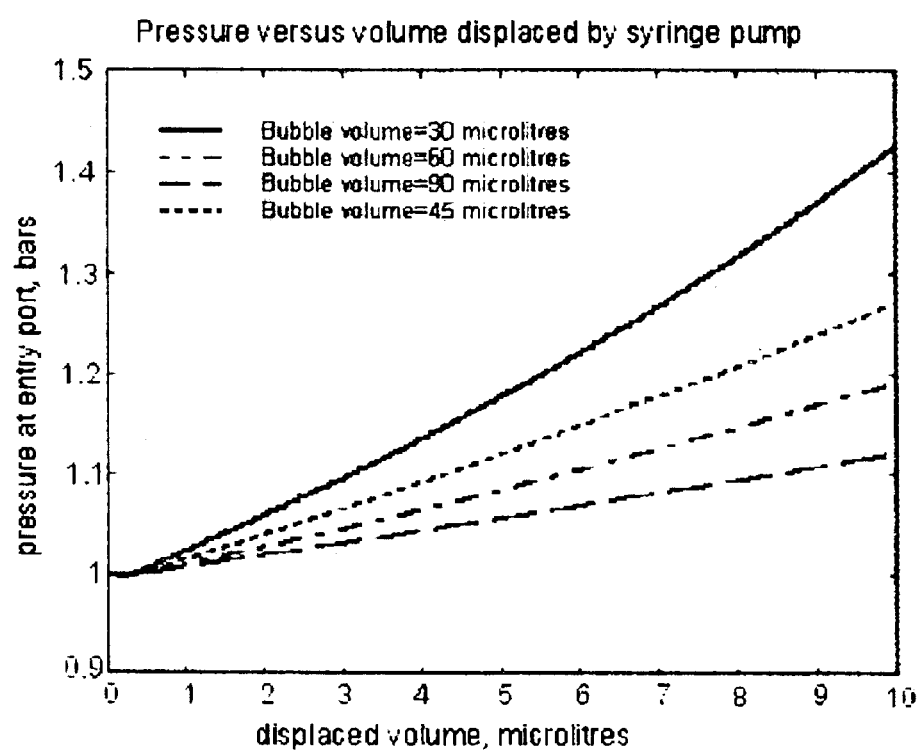
FIG. 4 is a graph showing further results of tests carried out.

FIG. 4 illustrates this for different volumes of air bubble. It will be seen from this that as the initial volume of the air bubble is increased, this causes a decrease in pressure at the entry port of the structure for the same displaced volume for the syringe pump. FIG. 4 shows clearly how one can determine the volume of the bubble and hence the expandability of the system by this calibration.

Figure 5:
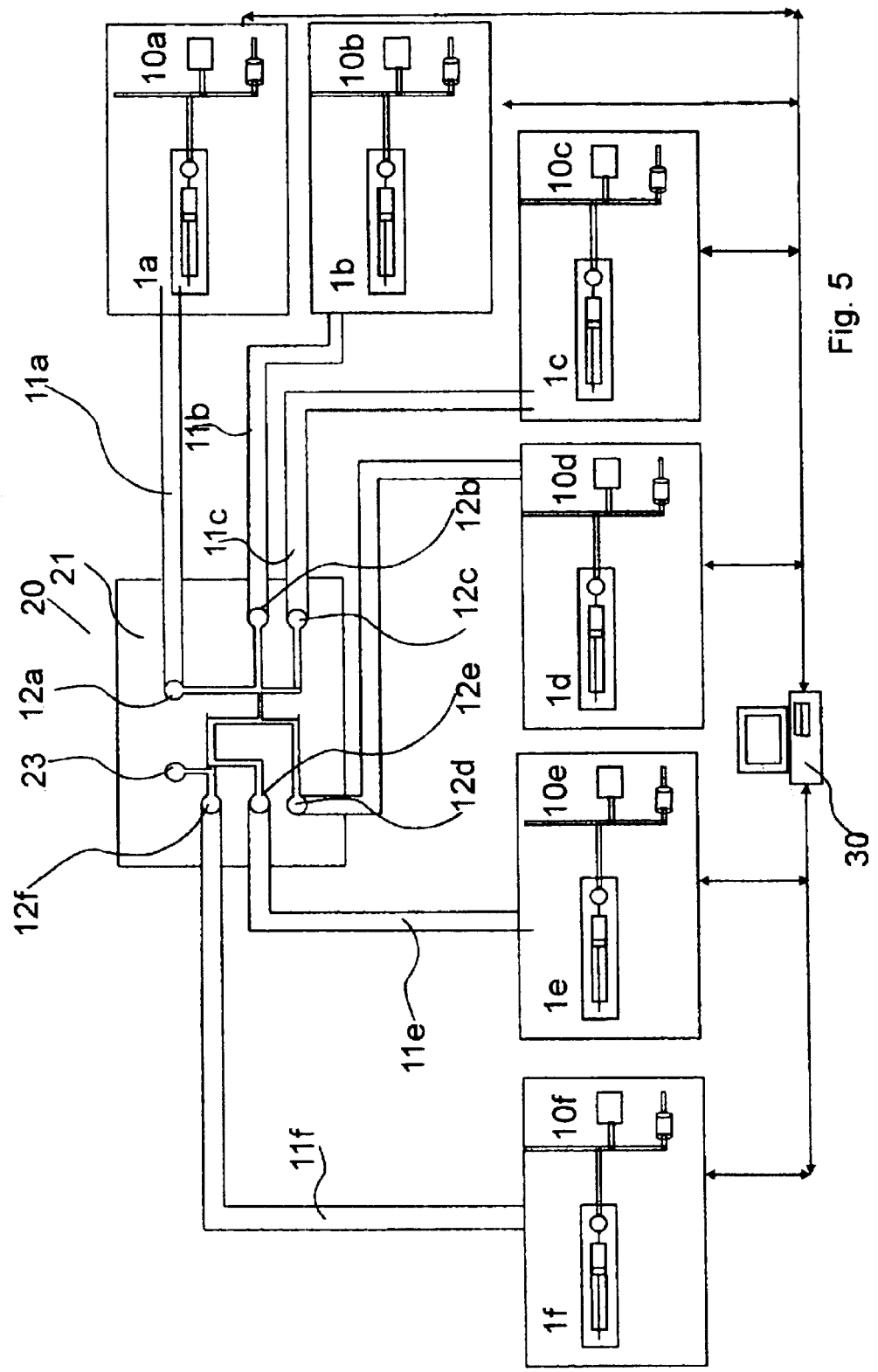
FIG. 5 is a schematic layout of another assembly according to the invention.

Referring to FIG. 5, there is illustrated an alternative construction of system according to the invention comprising a plurality of positive displacement pumps and associated liquid outlet link assemblies, all connected again to the same liquid outlet means, again of a microchannel structure assembly 21. In this embodiment, the liquid outlet link assemblies 10 are identified by various subscript letters, as is the conduit 11 and the liquid outlets 12. Thus, it can be seen that there are a plurality of pumps 1(a) to 1(f), associated liquid link assemblies 10(a) to 10(f) including conduits 11(a) to 11(f) with liquid outlets 12(a) to 12(f) respectively feeding into the microchannel structure assembly 21. Again, there is provided the controller 30 which now controls each of the pumps and each of the liquid link assemblies. Obviously, each of the liquid outlet link assemblies can be set appropriately to achieved the desired accuracy of flow control through the particular liquid outlet.

This arrangement allows the manipulation of various liquids in parallel. For example, it will be appreciated that multiple laminar flows can be established inside single channel of a microchannel structure by injecting different liquids from different input ports. This can be used for studies of biological samples and their interaction and response to different chemical reagents, especially for diagnostic purposes. It will be appreciated that some of the liquids injected may be chemical reagents. One or more of the liquid streams may contain biological samples such as cells, proteins, drug candidates and other chemical reagents. Such a multiple flow arrangement can be important when simulating human blood circulation and immune system response. The controlled mixing of liquids may also be possible in this configuration.

Referring now to FIGS. 6(a) and (b), there is illustrated a liquid outlet means, again identified by the reference numeral 20, in the form of a microchannel structure 21, in which parts similar to those described with reference to the previous drawings are identified by the same reference numerals, subscript letters being used to designate a multiplicity of, for example, liquid outlets 12 from various liquid link assemblies (not shown), each of which will in turn will be connected to its own positive displacement pump, again not shown. FIG. 6(a) shows a top view of a microchannel structure and FIG. 6(b) shows the front view cross-section through the point L—L. In this embodiment, as can be seen from FIG. 6(b), the microchannel 22 delivers to the exit port 23, three different liquids, identified by the letters A, B, and C and different hatching. These correspond to flows from the microchannels 22a, 22b and 22c. It will be appreciated that by suitable calibration of the pumps connected to the liquid outlets 12a, 12b, and 12c, the flow rates through the channels 22a, 22b and 22c can be manipulated. Thus, multiple laminar flow can be established inside the one microchannel 22 by injecting different liquids from different positive displacement pumps and associated liquid link assemblies. This can be used for studies on biological samples and their interaction and response to different chemical reagents. It will be appreciated that this would be particularly suitable, as mentioned above, for diagnostic purposes where one or more of the streams may contain biological samples such as cells and proteins and other chemical reagents. Needless to say, this arrangement can be used to check, for example, the efficacy of various drugs.

It will be appreciated that since the various positive displacement pumps can separately control the pressures at which the associated liquid link assemblies deliver the liquids through their liquid outlets and thus into the inlet of the various microchannels, it is possible to control the ratio at which several different liquids are mixed and therefore composition of the mixture. It is known that in microfluidic structures where flow is essentially laminar, mixing can occur only by diffusion. Thus, any mixing that will occur in the microchannel 22 of FIG. 6(b) will occur by diffusion. It will be appreciated, therefore, that depending on the velocity of the liquids and the length of the channel 22, total mixing of the liquids can be achieved by the time the exist port is reached.

Figure 6:
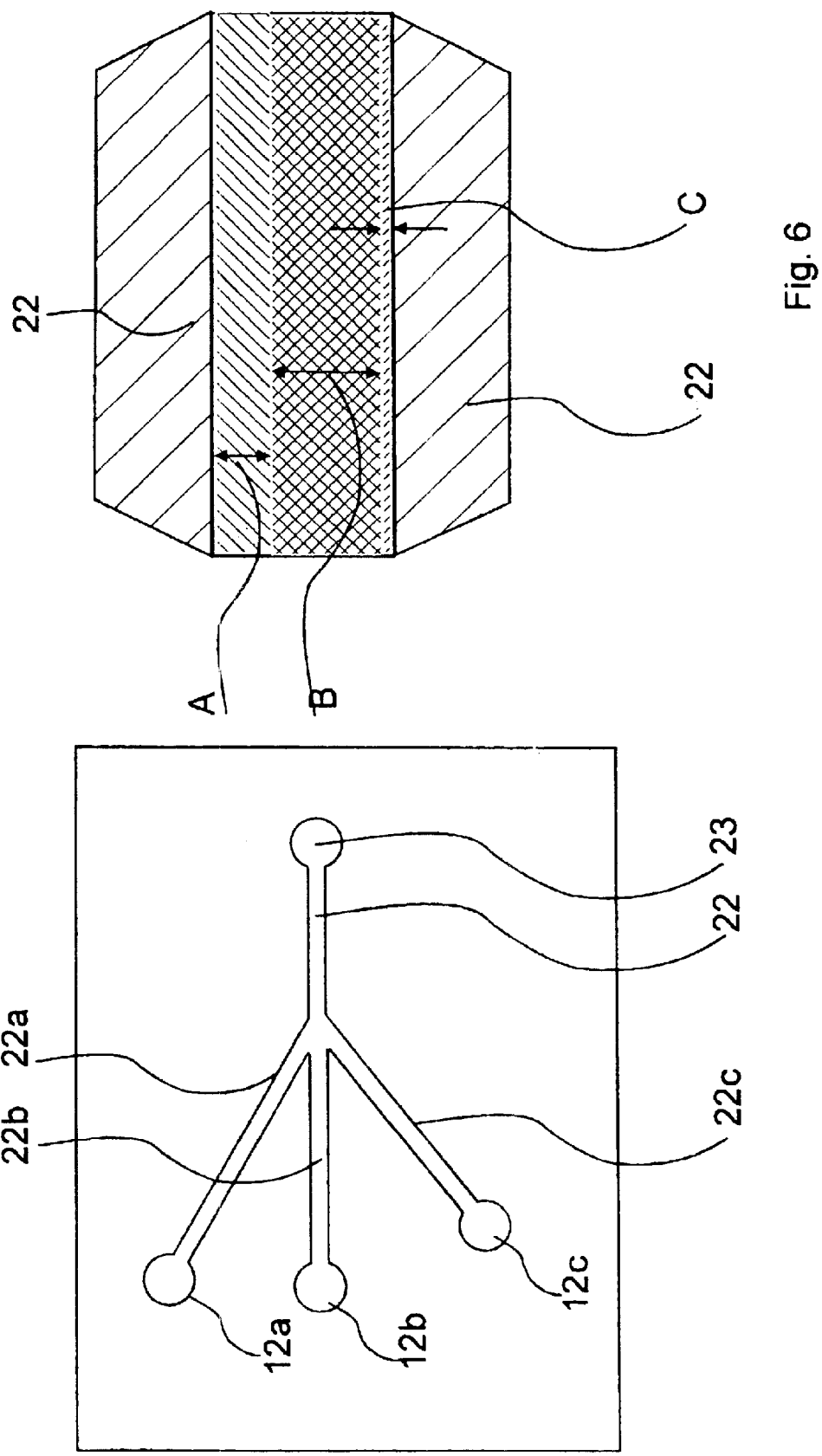
FIGS. 6(a) and (b) are layouts and sectional views of portion of a microchannel structure used in accordance with the invention.
Figure 7:
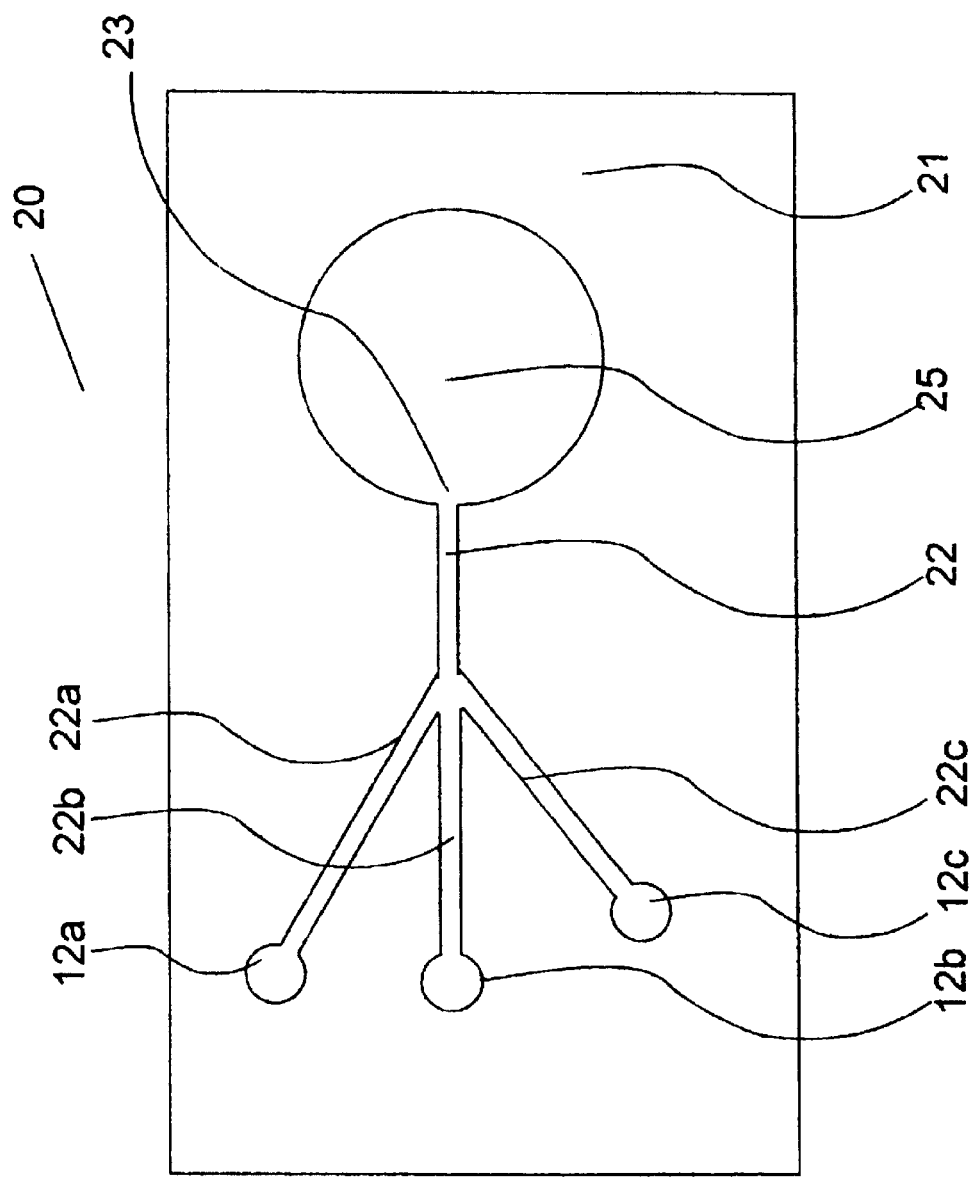
FIG. 7 is a plan view of another microchannel structure.

Referring to FIG. 7, there is identified a further liquid outlet means, again provided by a microchannel structure assembly 21, identical in all respects to the microchannel structure assembly 21 of FIG. 6 except that the exit port 23 feeds a mixing chamber 25.

Figure 8:
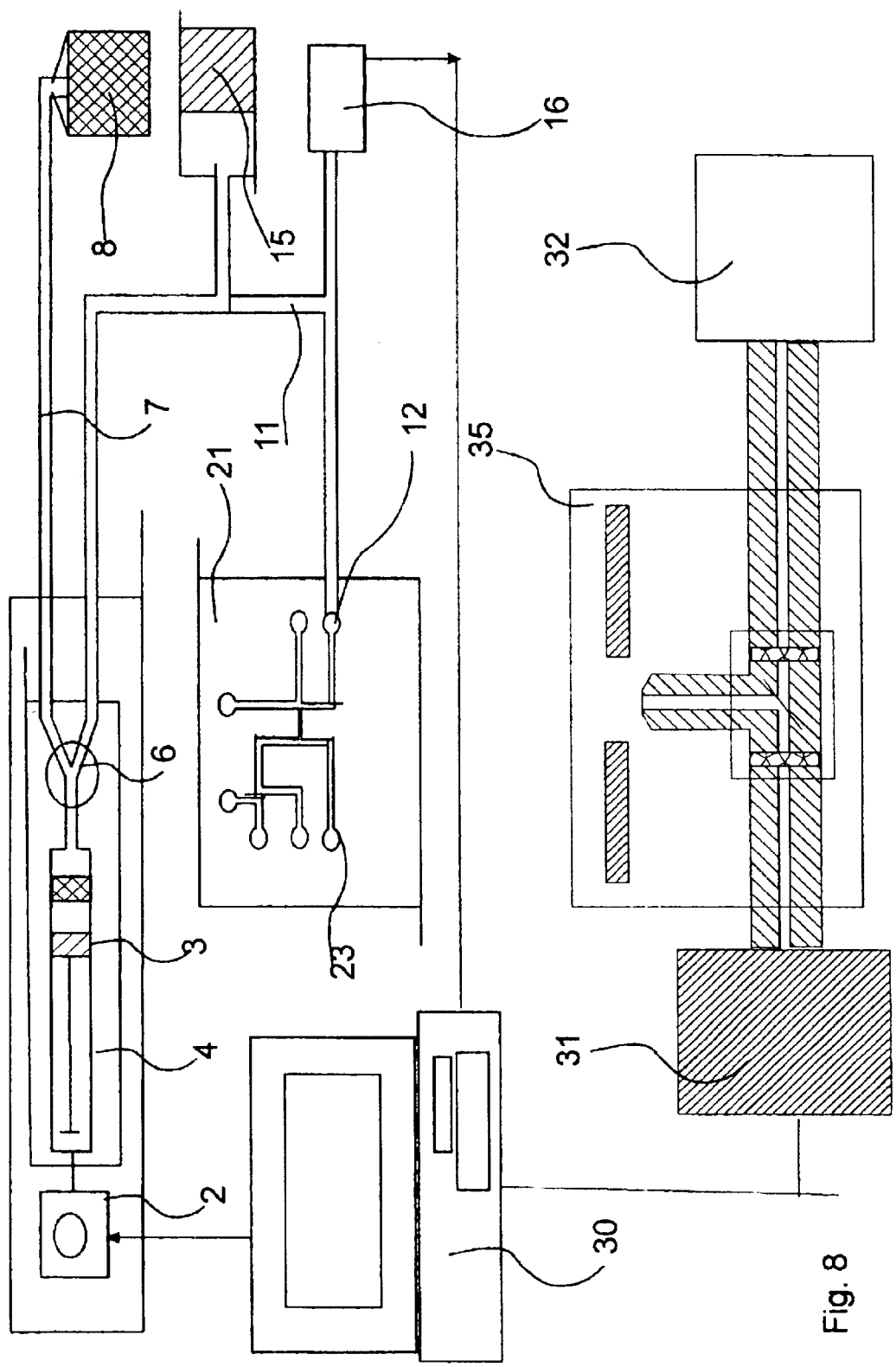
FIG. 8 is a schematic layout of a still further assembly according to the invention.

Referring now to FIG. 8, there is illustrated an assembly, most of which is identical to that illustrated in FIG. 1, in which parts similar to those described with reference to the previous drawing, are identified by the same reference numerals. In this embodiment, the controller 30 is connected to a video camera 31, in turn connected to a microscope assembly 35 which is also connected to an excitation source 32. The microscope assembly 35 and the video camera 31 provide an optical control feedback to the controller 30. The controller 30 which is essentially a computer based feedback system can incorporate the real time video data acquired. For example, injected liquids can be stained with different epifluorescent dyes and then the boundary between streams can be defined and controlled in real time by taking fluorescent level measurements, analysing this data for different streams and controlling pressures of the corresponding liquid outlets of the liquid outlet means. Thus, precise control of pumping can be achieved, as desired. For example, the arrangements illustrated in FIGS. 6 and 7 can be so arranged that the flow within the branched channels 22(a), 22(b) and 22(c) can be accurately controlled so that the multi-laminar flow is established as illustrated in FIG. 6. It will be appreciated that, depending on the pressure exerted and the flow, the boundary between the streams of liquids can be controlled very successfully by using the optical feedback.

Figure 9:
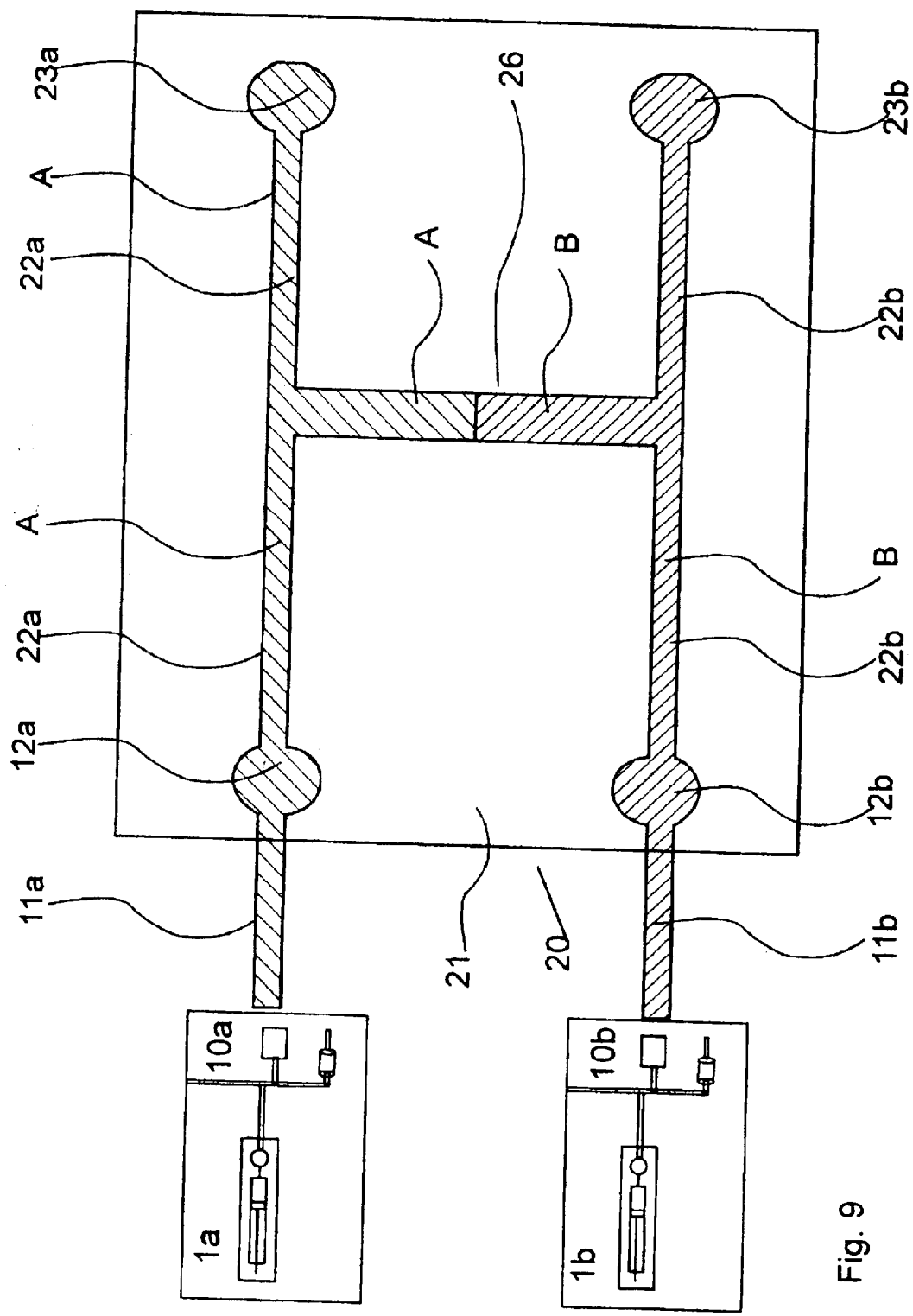
FIG. 9 is a view of another system according to the invention.

Referring now to FIG. 9, there is illustrated an alternative construction of liquid outlet means, again a microchannel structure assembly 21, and parts similar to those described with reference to the previous drawings are identified by the same reference numerals. In this embodiment, the two microchannels 22(a) and 22(b) are connected by a cross channel 26. The flows in the two separate microchannels 22(a) and 22(b) of the liquids, identified by the letters A and B, are controlled by their associated positive displacement pumps 1(a) and 1(b) and liquid link assemblies 10(a) and 10(b). Ideally, the liquids are stained with different fluorescent dyes. When a balanced condition is reached, there will be no flow in the cross channel 26 and therefore, either the liquid A or the liquid B will slowly diffuse through the cross channel 26 into one or other of the other channels 22(b) or 22(a), respectively. The two liquids A and B are schematically shown by different hatching.

Such a construction of microchannel 21 and the use of the system according to the present invention will allow the establishment of very small gradients of reagents which is very important for studies of cellular response and chemoattraction.

Figure 10:
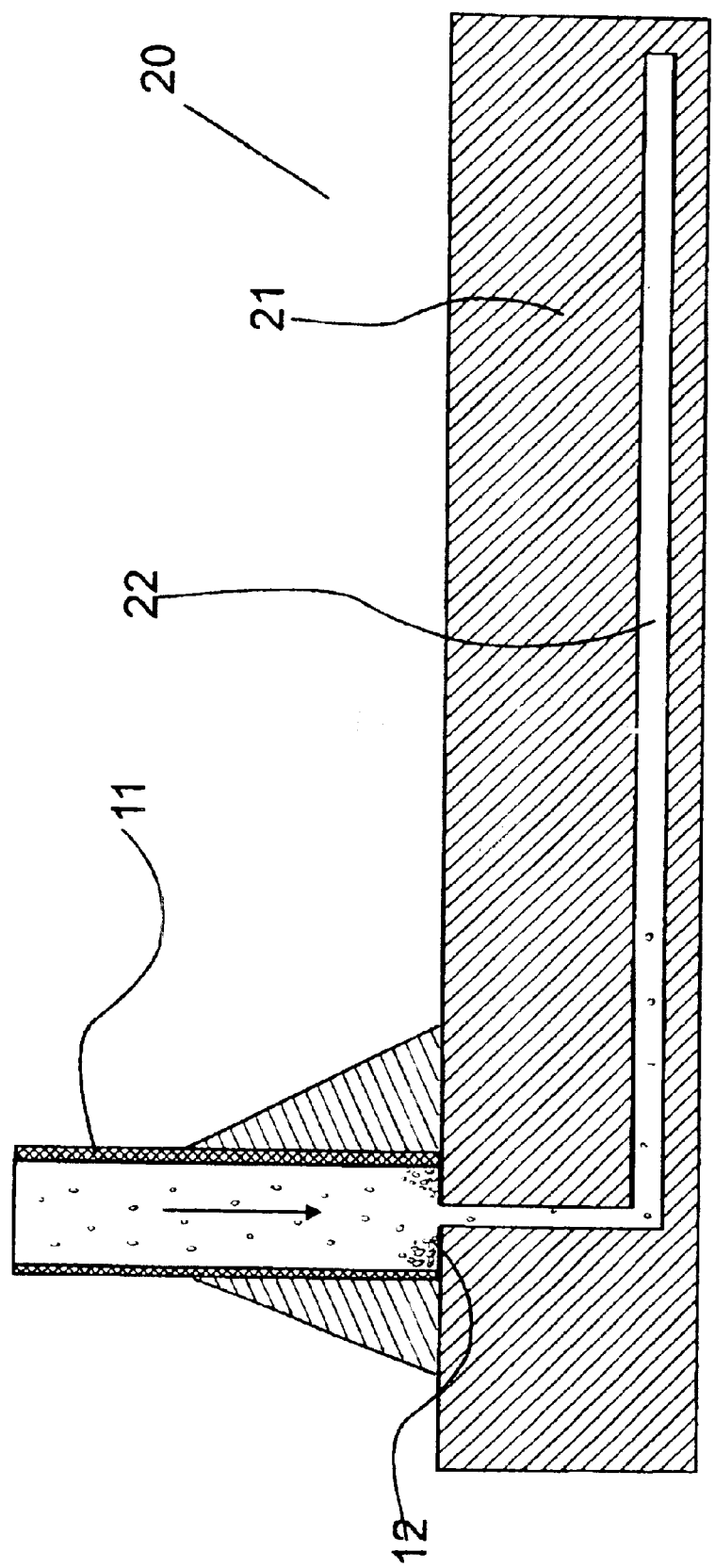
FIG. 10 is a sectional view through portion of a microchannel structure used with the invention.

Referring now to FIG. 10, there is illustrated portion of the conduit 11 feeding, through the liquid outlet 12, a microchannel 22 of a microchannel structure assembly 21 forming a liquid outlet means 20.

It will be appreciated that if the diameter of the conduit 11 is a factor n greater than the diameter of the microchannel 22, then the velocity in the conduit 11 will be $n^2$ lower than that in the microchannel 22. Thus, for example, if the velocity in the microchannel is to be of the order of 10 to 100 micrometers/sec and the ratio of diameters is 10, that is to say n=10, then the flow velocity at the liquid outlet 12 will be of the order of 1000 nanometers to 100 nanometer/sec. In many situations, this will not be of any great importance, however, if it is required to transport particles in suspensions such as biological cells, which particles in suspension have a density greater than that of the carrier liquid, then an aggregation or collection of these particles will occur at the bottom of the conduit 11 adjacent the liquid outlet 12. This collection of particles occurs because the velocity of sinking, which can be found from considering forces applied to the cell, namely the gravitational force minus the Archimedes force minus the Stokes drag force, dominates the velocity of fluid movement. Therefore, some cells which are close to the inlet tubing wall, that is to say, the conduit 11 in the embodiments above, reach the bottom at the liquid outlet 12 before entering the microchannel entrance. Such an accumulation of cells at the liquid outlet can cause a reduction in the cell concentration inside the microchannel compared to the initial concentrations. This reduction could be significant.

Figure 11:
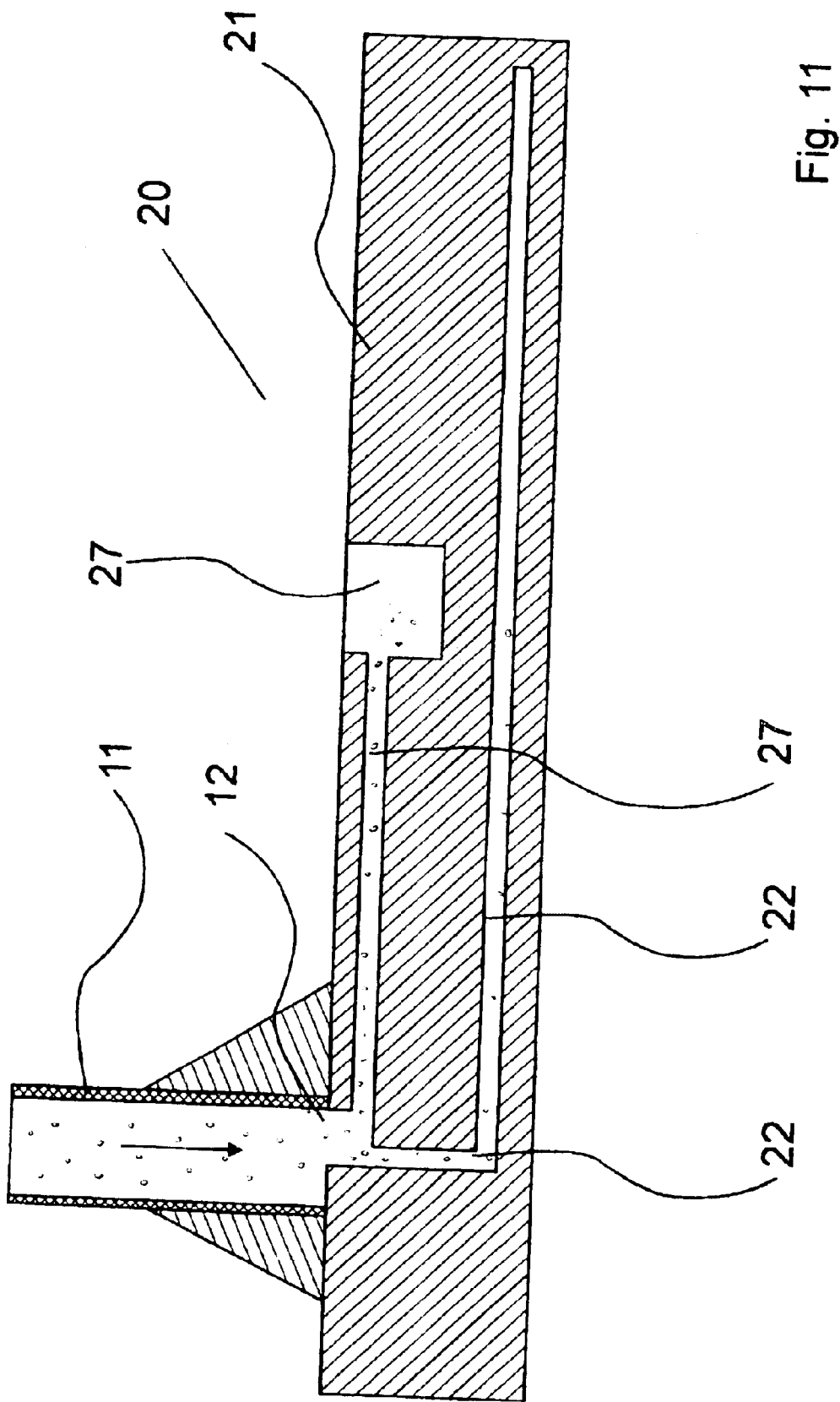
FIG. 11 is a sectional view through another microchannel structure.

Referring now to FIG. 11, there is illustrated an alternative construction of liquid outlet means, again indicated generally by the reference numeral 20, and formed from a microchannel structure 21 in which there is an additional compensation channel 27 at the liquid outlet 12. This compensation channel 27 is so arranged such that the cross sectional area of the compensation channel 27 and of the microchannel 22 roughly equal the cross sectional area of the conduit 11. This will then result in a homogeneous flow with equal velocity in both the inlet port to the microchannel, that is to say, the liquid outlet 12 and in the microchannel. The additional liquid can be disposed out the microchannel or can be recirculated.

While in the embodiment described in FIG. 11, the compensation channel 27 has been illustrated as a portion of the microchannel structure assembly 21, it will be appreciated that the liquid outlet 12 could be so arranged that itself had a recirculation conduit adjacent the liquid outlet such as to balance the flow rates.

The delivery of the sample to microfluidic microchannel structures can be a difficult task. Typically, in the microfluidic system, the diameter of the microchannels is an order of magnitude lower or more than the diameter of the inlet port and tubing delivering the sample. To allow optical observation of biological samples, the linear velocity of the liquid inside the channel should be relatively small, in the range of micrometers/sec.

Referring now to FIG. 12, substantially the same method can be used in the case where a wider microchannel 22 is connected to a narrower microchannel 28 which will cause the concentration of cells in the narrow channel to be less than the initial concentration of cells in the wider channels. This will happen again due to the aggregation of cells around the input from the wider channel 22 into the narrow channel 28 or by settlement along the channel 22. This can be overcome by the use of a further compensation channel 29 such that the cross sectional area of the compensation channel 29 and the narrow channel 28 roughly equal the cross sectional area of the wider microchannel 22.

In the specification the terms "comprise, comprises, comprised and comprising" or any variation thereof and the terms "include, includes, included and including" or any variation thereof are considered to be totally interchangeable and they should all be afforded the widest possible interpretation.

The invention is not limited to the embodiments hereinbefore described but may be varied in both construction and detail.

What is claimed is:

1. A liquid outlet link assembly to provide a steady liquid delivery output rate below 10 µl/minute through a liquid outlet means from a positive displacement pump having an immediate step pumping rate which is relatively substantially larger than the delivery rate through the liquid outlet means comprising:
   a body having a hollow interior;
   a liquid inlet in the body of the link assembly for connection to the pump;
   a liquid outlet in the body for connection to the liquid outlet means, said outlet means comprising a microchannel whereby a resistance to flow to the liquid outlet means is substantially greater than through the hollow interior of the body; and
   pressure compressible means which contracts to reduce the pressure surge of a liquid within the body when the liquid is delivered by the pump at an increased pressure through the liquid inlet, and then gradually expands to decrease the pressure drop of the liquid within the body as it is delivered through the liquid outlet, so as to maintain a substantially steady liquid pressure at the liquid outlet.

2. The assembly as claimed in claim 1, in which the pressure compressible means comprises a gas bubble.

3. The assembly as claimed in claim 2, in which the volume of the gas bubble is multiple of the volume of liquid dispensed in one step of the pump.

4. The assembly as claimed in claim 2, in which the expansion means comprises more than one gas bubble and the aggregate volume of the bubbles is a multiple of the volume of liquid dispensed in one step of the pump.

5. The assembly as claimed in claim 2, in which the liquid outlet means comprises an elongate microchannel structure, the liquid pressure is such as to provide the necessary liquid pressure gradient between an entry port formed by the proximal end of the microchannel structure for connection to the liquid outlet and an exit port formed by the distal end of the microchannel structure.

6. The assembly as claimed in claim 2 in which control means are provided, the control means comprising:
   means for sensing the flow conditions within the liquid outlet means; and
   means for causing the pump to operate in response to the sensed flow conditions.

7. The assembly as claimed in claim 1, in which the pressure activated expansion means comprises an elastic membrane forming part of the body member.

8. The assembly as claimed in claim 1, in which the body comprises expandable tubing which forms the expansion means.

9. The assembly as claimed in claim 1, in which the liquid outlet means comprises an elongate microchannel structure, the liquid pressure is such as to provide the necessary liquid pressure gradient between an entry port formed by the proximal end of the microchannel structure for connection to the liquid outlet and an exit port formed by the distal end of the microchannel structure.

10. The assembly as claimed in claim 1, in which control means are provided, the control means comprising:
    means for sensing the flow conditions within the liquid outlet means; and
    means for causing the pump to operate in response to the sensed flow conditions.

11. The assembly as claimed in claim 1, in which the liquid outlet in the body includes liquid take-off means whereby the flow rates of the liquid in the liquid link assembly and the liquid outlet means are substantially equal.

12. The assembly as claimed in claim 1, in which the liquid outlet in the body includes a recirculation pipe connected between the liquid outlet and the body.

13. A liquid outlet link assembly to provide a steady liquid delivery output rate below 10 µl/minute through a liquid outlet means from a positive displacement pump having an immediate step pumping rate which is relatively substantially larger than the delivery rate through the liquid outlet means comprising:
    a body having a hollow interior;
    a liquid inlet in the body of the link assembly for connection to the pump;
    a liquid outlet in the body for connection to the liquid outlet means, said outlet means comprising a microchannel whereby a resistance to flow to the liquid outlet means is substantially greater than through the hollow interior of the body; and
    a gas bubble in the body to create a liquid pressure at the liquid outlet o provide the desired liquid delivery flow rate through the liquid outlet means.

14. The assembly as claimed in claim 11, in which the volume of the gas bubble is multiple of the volume of liquid dispensed in one step of the pump.

15. The assembly as claimed in claim 11, in which the liquid outlet means comprises an elongate microchannel structure, the liquid pressure is such as to provide the necessary liquid pressure gradient between an entry port formed by the proximal end of the microchannel structure for connection to the liquid outlet and an exit port formed by the distal end of the microchannel structure.

16. The assembly as claimed in claim 11, in which the liquid outlet in the body includes liquid take-off means whereby the flow rates of the liquid in the liquid link assembly and the liquid outlet means are substantially equal.

17. The assembly as claimed in claim 1, in which the liquid outlet in the body includes a recirculation pipe connected between the liquid outlet and the body.

18. A pump assembly to provide a steady liquid delivery output rate below 10 µl/minute comprising:
    a positive displacement pump;
    a motor to operate the pump in a stepped manner such that the pump has an immediate step pumping rate which is relatively substantially larger than the liquid delivery output rate;
    a liquid outlet means for the pump assembly;
    a liquid outlet link assembly comprising:
      a body having a hollow interior;
      a liquid inlet in the body of the link assembly for connection to the pump;
      pressure activated expansion means in the body to create a liquid pressure at the liquid outlet to provide the desired liquid delivery flow rate through the liquid outlet means.

19. The pump assembly as claimed in claim 18, in which the expansion means comprises a gas bubble.

20. The pump assembly as claimed in claim 18, in which the volume of the gas bubble is multiple of the volume of liquid dispensed in one step of the pump.

21. The pump assembly as claimed in claim 18, in which the expansion means comprises more than one gas bubble and the aggregate volume of the bubbles is a multiple of the volume of liquid dispensed in one step of the pump.

22. The pump assembly as claimed in claim 18, in which the pressure activated expansion means comprises an elastic membrane forming part of the body member.

23. The pump assembly as claimed in claim 18, in which the liquid outlet means comprises an elongate microstructure, the liquid pressure is such as to provide the necessary liquid pressure gradient between the entry port formed by the proximal end of the microstructure and the exit port formed by the distal end of the microstructure.

24. The pump assembly as claimed in claim 18, in which control means are provided, the control means comprising:
means for sensing the flow conditions within the liquid outlet means; and
means for causing the pump to operate in response to the sensed flow conditions.

25. The pump assembly as claimed in claim 18, comprising:
optical flow monitoring means connected to the liquid outlet means; and
control means connected to the optical flow monitoring means and the pump to operate the pump to provide the desired flow rate through the liquid outlet means.

26. The pump assembly as claimed in claim 18, comprising pressure sensing means in the liquid outlet means and control means for operative connection to the positive displacement pump to cause the pump to operate on the pressure falling below a predetermined level.

27. The pump assembly as claimed in claim 18, in which the pump is a syringe pump.

28. The pump assembly as claimed in claim 18, in which the volume pumped for each step of the syringe pump is greater than 0.1 $\mu l$.

29. The pump assembly as claimed in claim 18, in which the volume pumped for each step of the syringe pump is of the order of 0.2 $\mu l$.

30. The pump assembly as claimed in claim 18, comprising at least two syringe pumps feeding the one liquid outlet link assembly.

31. The pump assembly as claimed in claim 18, in which the volume dispensed by at least one of the pumps for one step of that pump is substantially less than that of the other pumps.

32. The pump assembly as claimed in claim 18, in which at least one additional electrokinetic pump is provided.

33. The pump assembly as claimed in claim 32, in which the electrokinetic pump is an electroosmotic pump.

34. The pump assembly as claimed in claim 32, in which the electrokinetic pump is an electrohydrodynamic pump.

35. The pump assembly as claimed in claim 18, in which the liquid outlet in the body includes liquid take-off means whereby the flow rates of the liquid in the liquid link assembly and the liquid outlet means are substantially equal.

36. The pump assembly as claimed in claim 18, in which the liquid outlet of the body includes a recirculation pipe connected between the liquid outlet and the body.

37. A microchannel structure assembly for the controlled flow of small volumes of liquids comprising:
an elongate enclosed microchannel structure having an internal bore less than 1000 $\mu m^2$ cross-sectional area;
a positive displacement pump operating in a series of steps, each step operation of the pump dispensing a volume of the order of 0.01 $\mu l$;
a liquid outlet link assembly comprising a body having a hollow interior with a bore considerably larger than the microchannel structure bore and thus preventing a resistance to flow therethrough substantially less than through the microchannel structure;
a liquid inlet in the body of the link assembly for connection to the pump;
a liquid outlet in the body of the link assembly for connection to the microchannel structure; and
pressure activated expansion means in the body of the link assembly to create a liquid pressure at the liquid outlet to provide the desired liquid delivery output rate from the liquid outlet means.

38. The microchannel structure assembly as claimed in claim 37, in which the expansion means comprises a gas bubble.

39. The microchannel structure assembly as claimed in claim 37, in which the volume of the gas bubble is multiple of the volume of liquid dispensed in one step of the pump.

40. The microchannel structure assembly as claimed in claim 37, in which the expansion means comprises more than one gas bubble and the aggregate volume of the bubbles is a multiple of the volume of liquid dispensed in one step of the pump.

41. The microchannel structure assembly as claimed in claim 37, in which at least portion of the body of the link assembly is expandable tubing which forms the expansion means.

42. The microchannel structure assembly as claimed in claim 37, in which the pressure activated expansion means comprises an elastics membrane forming part of the body member.

43. The microchannel structure assembly as claimed in claim 37, in which control means are provided, the control means comprising:
means for sensing the flow conditions within the liquid outlet means; and
means for causing the pump to operate in response to the sensed flow conditions.

44. The microchannel structure assembly as claimed in claim 37, comprising:
optical flow monitoring means connected to the liquid outlet means; and
control means connected to the optical flow monitoring means and the pump to operate the pump to provide the desired flow rate through the liquid outlet means.

45. The microchannel structure assembly as claimed in claim 37, comprising pressure sensing means in the liquid outlet and control means for operative connection to the positive displacement pump to cause the pump to operate on the pressure falling below a predetermined level.

46. The microchannel structure assembly as claimed in claim 37, comprising at least two syringe pumps feeding the one liquid outlet link assembly.

47. The microchannel structure assembly as claimed in claim 37, in which the volume dispensed by at least one of the pumps for one step of that pump is substantially less than that of the other pumps.

48. The microchannel structure assembly as claimed in claim 37, in which the pump is a syringe pump.

49. The microchannel structure assembly as claimed in claim 37, in which at least one additional electrokinetic pump is provided.

50. The microchannel structure assembly as claimed in claim 49, in which the electrokinetic pump is an electroosmotic pump.

51. The microchannel structure assembly as claimed in claim 49, in which the electrokinetic pump is an electrohydrodynamic pump.

52. The microchannel structure assembly as claimed in claim 37, in which adjacent the liquid outlet of the liquid outlet link assembly, there is provided a flow balancing conduit, the cross-sectional area of the body adjacent the inlet substantially equaling the aggregate cross-sectional area of the microchannel structure and the recirculation conduit.

53. The microchannel structure assembly as claimed in claim 37, the liquid outlet in the body includes liquid take-off means whereby the flow rates of the liquid in the liquid link assembly and the microchannel structure are substantially equal.

54. The microchannel structure assembly as claimed in claim 37, in which the liquid of the body includes a recirculation pipe connected between the liquid outlet and the body.

\* \* \* \* \*